(12) United States Patent
Kashiwagi (10) Patent No.: US 11,931,232 B2
(45) Date of Patent: Mar. 19, 2024

(54) ABSORBENT ARTICLE

(71) Applicant: DAIO PAPER CORPORATION, Shikokuchuo (JP)

(72) Inventor: Tatsuhiko Kashiwagi, Sakura (JP)

(73) Assignee: DAIO PAPER CORPORATION, Shikokuchuo (JP)

( * ) Notice: Subject to any disclaimer, the term of this patent is extended or adjusted under 35 U.S.C. 154(b) by 909 days.

(21) Appl. No.: 16/964,338

(22) PCT Filed: Mar. 28, 2019

(86) PCT No.: PCT/JP2019/013604
§ 371 (c)(1),
(2) Date: Jul. 23, 2020

(87) PCT Pub. No.: WO2019/189575
PCT Pub. Date: Oct. 13, 2019

(65) Prior Publication Data
US 2021/0069027 A1    Mar. 11, 2021

(30) Foreign Application Priority Data

Mar. 30, 2018 (JP) ................. 2018-067199

(51) Int. Cl.
*A61F 13/475* (2006.01)
*A61F 13/533* (2006.01)
*A61F 13/53* (2006.01)

(52) U.S. Cl.
CPC ........ *A61F 13/4756* (2013.01); *A61F 13/533* (2013.01); *A61F 2013/530481* (2013.01)

(58) Field of Classification Search
CPC ................ A61F 13/4756; A61F 13/533; A61F 2013/530481; A61F 13/49413;
(Continued)

(56) References Cited

U.S. PATENT DOCUMENTS 6,416,502 B1 * 7/2002 Connelly ............... A61F 13/532
   604/389
7,438,708 B2 * 10/2008 Kashiwagi ............ A61F 13/515
   604/385.03
(Continued)

FOREIGN PATENT DOCUMENTS

CN   205626288 U   10/2016
EP   0 145 080 A2   6/1985
(Continued)

OTHER PUBLICATIONS

Extended European Search Report dated Mar. 31, 2021, in connection with corresponding EP Application No. 19776130.7; 14 pages.
(Continued)

*Primary Examiner* — Nicholas J. Weiss
*Assistant Examiner* — Brandon W. Levy
(74) *Attorney, Agent, or Firm* — Maier & Maier, PLLC (57) ABSTRACT

To enable an absorbent article to fit easily around the legs when worn and to improve fit. A pad which includes a polymer sheet having a superabsorbent polymer disposed between two nonwoven fabric sheets. Planar-shaped linear embossed grooves that protrude inward in a width direction from each side edge are formed at positions of the polymer sheet on which the groin of a wearer abuts when worn.
(Continued)

Standing gathers that rise along a longitudinal direction on a skin side are formed on both side portions on the skin side. Regions that are surrounded by the embossed grooves tend to deform around the legs with the embossed grooves as flexible shafts, so that the polymer sheet fits easily around the legs when worn and fit is improved.

4 Claims, 7 Drawing Sheets

(58) Field of Classification Search
CPC ............... A61F 13/532; A61F 13/4704; A61F 13/49001; A61F 13/536; A61F 13/539; A61F 13/53
See application file for complete search history.

(56) References Cited

U.S. PATENT DOCUMENTS

| | | | | |
|---|---|---|---|---|
| 2003/0093054 A1* | 5/2003 | Sierri | ............... | A61F 13/47263 604/385.04 |
| 2006/0041240 A1* | 2/2006 | Erdman | ............ | A61F 13/49413 604/385.28 |
| 2006/0069371 A1* | 3/2006 | Ohashi | ............... | A61F 13/4704 604/385.101 |
| 2013/0079741 A1* | 3/2013 | Nakashita | ......... | A61F 13/15707 493/395 |
| 2014/0163502 A1* | 6/2014 | Arizti | .................... | A61F 13/538 604/385.101 |
| 2016/0235595 A1* | 8/2016 | Ehrnsperger | .......... | A61F 13/536 |

FOREIGN PATENT DOCUMENTS

| | | |
|---|---|---|
| JP | 8-322875 A | 12/1996 |
| JP | 2008-79750 A | 4/2008 |
| JP | 2010-88528 A | 4/2010 |
| JP | 2011-229853 A | 11/2011 |
| JP | 2012-10980 A | 1/2012 |
| JP | 2012-125354 A | 7/2012 |
| JP | 2016-515458 A | 5/2016 |
| JP | 2017-29353 A | 2/2017 |
| JP | 2017-148389 A | 8/2017 |

OTHER PUBLICATIONS

Chinese Office Action dated Jun. 15, 2021, in connection with corresponding CN Application No. 201980012381.6 (11 pp., including machine-generated English translation).

Japanese Office Action dated Dec. 5, 2018, in connection with corresponding JP Application No. 2018-067199 (8 pp., including machine-generated English translation).

Translation of International Search Report dated Jun. 25, 2019 and Written Opinion of corresponding application No. PCT/JP2019/013604; 10 pgs.

* cited by examiner

ABSORBENT ARTICLE

FIELD

The present disclosure relates to an absorbent article such as a disposable diaper, a sanitary napkin, a panty liner, or an incontinence pad, and more particularly to an absorbent article including a polymer sheet that easily fits around legs.

BACKGROUND

Conventionally, as the absorbent article, there has been known an absorbent article in which an absorbent body having a function of absorbing and retaining a body fluid is interposed between a liquid-impermeable back sheet such as a polyethylene sheet or a polyethylene sheet laminated nonwoven fabric and a liquid-permeable face sheet such as a nonwoven fabric or a liquid-permeable plastic sheet.

A number of improvements have been made to this type of absorbent article, and it has been proposed that the absorbent article be provided with a polymer sheet in which a granular superabsorbent polymer is disposed between two sheets. Since the polymer sheet is thin by not including pulp fibers, there are advantages that there is no feeling of stiffening during wearing, and that concaves and convexes of the absorbent article become difficult to see from the outside of the clothing during wearing (outerwear is not affected). However, even though the polymer sheet is excellent in absorbing and retaining a large amount of body fluid, since an aggregate of powdery granular superabsorbent polymers is arranged inside, there is a problem that it is difficult to stably carry the superabsorbent polymers between two sheets. In addition, when around-leg cut lines notched on both side portions of the polymer sheet is provided to make it easier to fit around legs of a wearer during wearing, there is a problem that the superabsorbent polymer spills from a cut surface.

Examples of the absorbent article using such a polymer sheet include Patent Documents 1 and 2 below. Patent Document 1 below discloses an absorbent pad including a first nonwoven fabric layer, a second nonwoven fabric layer partially bonded to the first nonwoven fabric layer, an absorbent core disposed between the first nonwoven fabric layer and the second nonwoven fabric layer, and a plurality of seals connecting the first nonwoven fabric layer to the second nonwoven fabric layer.

In addition, Patent Document 2 below discloses a polymer sheet partitioned into a plurality of polymer-encapsulated cells in which a superabsorbent polymer is encapsulated inside by a bonded portion that bonds an upper layer sheet and a lower layer sheet.

Patent Document 1: JP-T-2016-515458 (the term "JP-T" as used herein means a published Japanese translation of a PCT patent application)

Patent Document 2: JP-A-2017-29353

SUMMARY

However, in any of the above-mentioned Patent Documents 1 and 2, the superabsorbent polymer is disposed between the two sheets and partitioning into the plurality of polymer-encapsulated cells is performed by the bonded portion bonding the two sheets. However, a structure for easily fitting around the legs during wearing is not achieved.

Therefore, a main problem of the invention is to provide an absorbent article that easily fits around the legs during wearing and improves fit.

To solve the above problem, there is provided an absorbent article including a polymer sheet in which a superabsorbent polymer is disposed between two nonwoven fabric sheets, characterized in that linear embossed grooves having a planar shape protruding inward in a width direction from both side edges, respectively, are formed at positions of the polymer sheet with which a groin of a wearer comes into contact during wearing.

In the invention, since linear embossed grooves having a planar shape protruding inward in a width direction from both side edges, respectively, are formed at positions of a polymer sheet with which a groin of a wearer comes into contact during wearing in the polymer sheet in which a superabsorbent polymer is disposed between two nonwoven fabric sheets, regions surrounded by the embossed grooves are easily deformed along the legs using the embossed grooves as flexible shafts, the polymer sheet easily fit around the legs during wearing, and fit is improved.

According to the invention, there is provided the absorbent article, in which three-dimensional gathers standing up to a skin side along a longitudinal direction are provided at both side portions on a skin side.

According to the invention, the three-dimensional gathers standing up to the skin side along the longitudinal direction are provided at both side portions on the skin side, respectively, the regions surrounded by the embossed grooves easily rise to the skin side by being bent inward using the embossed grooves as flexible shafts due to a contraction force along the longitudinal direction of the three-dimensional gathers, and both side portions of the polymer sheet are more easily deformed around the legs. For this reason, the polymer sheet easily fits around the legs during wearing, and the fit is improved.

According to the invention, there is provided the absorbent article, in which the superabsorbent polymer is disposed in regions surrounded by the embossed grooves on both sides of the polymer sheet, respectively.

In the invention, the superabsorbent polymer is disposed in regions surrounded by the embossed grooves on both sides of the polymer sheet, respectively, the regions fit around the legs and can absorb the body fluid.

In the invention, there is provided the absorbent article, in which in the regions surrounded by the embossed grooves on both sides of the polymer sheet, respectively, the superabsorbent polymer is not disposed, and a middle-layer nonwoven fabric sheet is disposed between the two nonwoven fabric sheets.

In the invention, the superabsorbent polymer is not disposed, and a middle-layer nonwoven fabric sheet is disposed between the two nonwoven fabric sheets in the regions surrounded by the embossed grooves on both sides of the polymer sheet, respectively, cushioning around the legs can be ensured, and an excellent feeling of wearing can be obtained.

In the invention, there is provided the absorbent article, in which in the regions surrounded by the embossed grooves on both sides of the polymer sheet, respectively, the superabsorbent polymer is not disposed, and the two nonwoven fabric sheets are directly bonded together.

In the invention, the superabsorbent polymer is not disposed, and the two nonwoven fabric sheets are directly bonded together in the regions surrounded by the embossed grooves on both sides of the polymer sheet, respectively, the regions are easily deformed, and fit around the legs can be further improved.

In the invention, there is provided the absorbent article, in which in the regions surrounded by the embossed grooves on both sides of the polymer sheet, respectively, around-leg cut lines notched on both side portions of the polymer sheets are provided.

In the invention since around-leg cut lines are provided in the regions surrounded by the embossed grooves on both sides of the polymer sheet, respectively, the polymer sheet is more reliably fit around the legs.

As described in detail above, according to the invention, it is possible to easily fit around the legs during wearing and improve fit.

DETAILED DESCRIPTION

MODE FOR CARRYING OUT THE INVENTION

Hereinafter, an embodiment of the invention will be described in detail with reference to the drawings.

<Example of Basic Structure of Pad>

Figure 1:
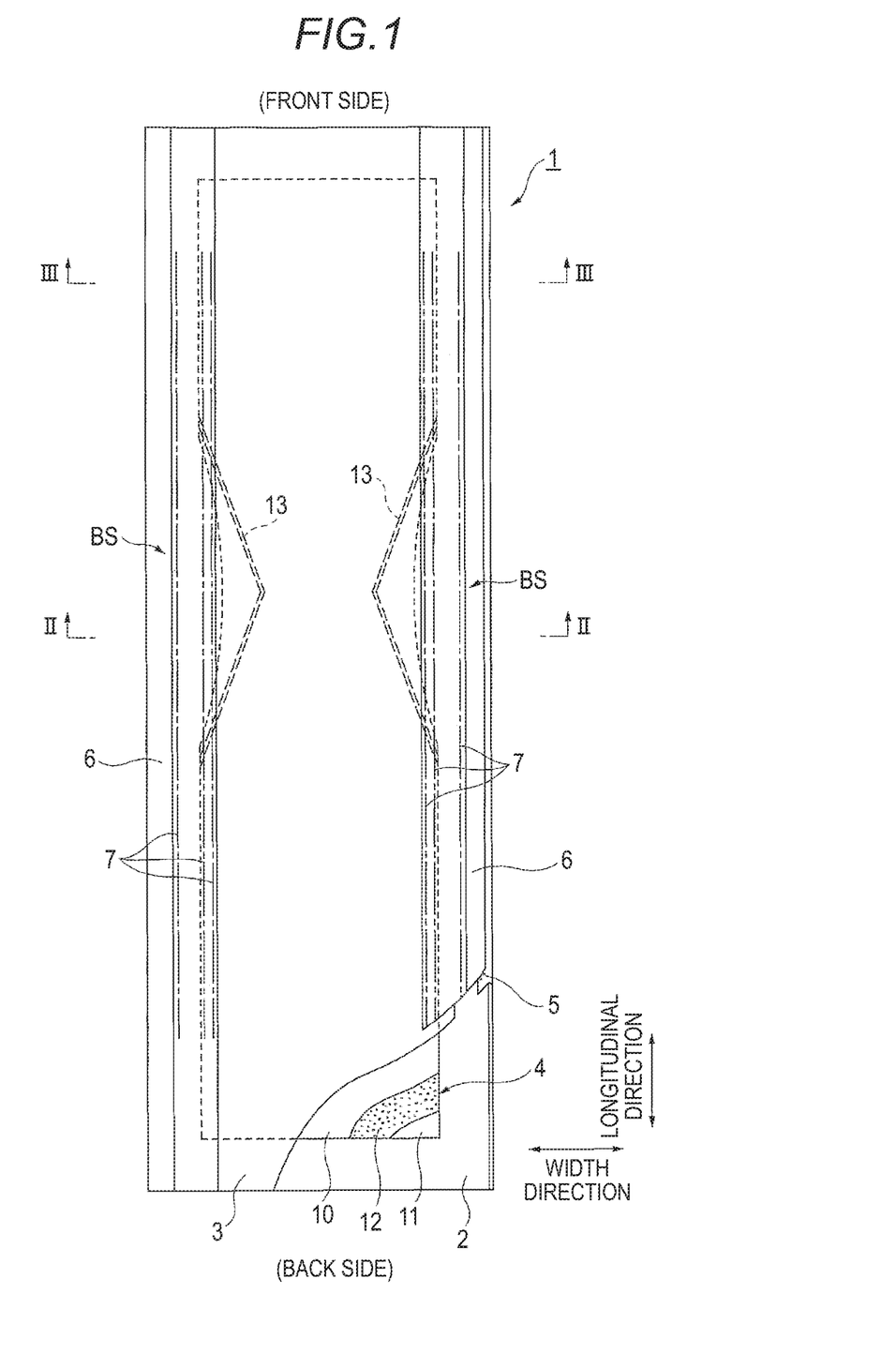
FIG. 1 is a partially broken development diagram of a pad 1 according to the invention.
Figure 2:
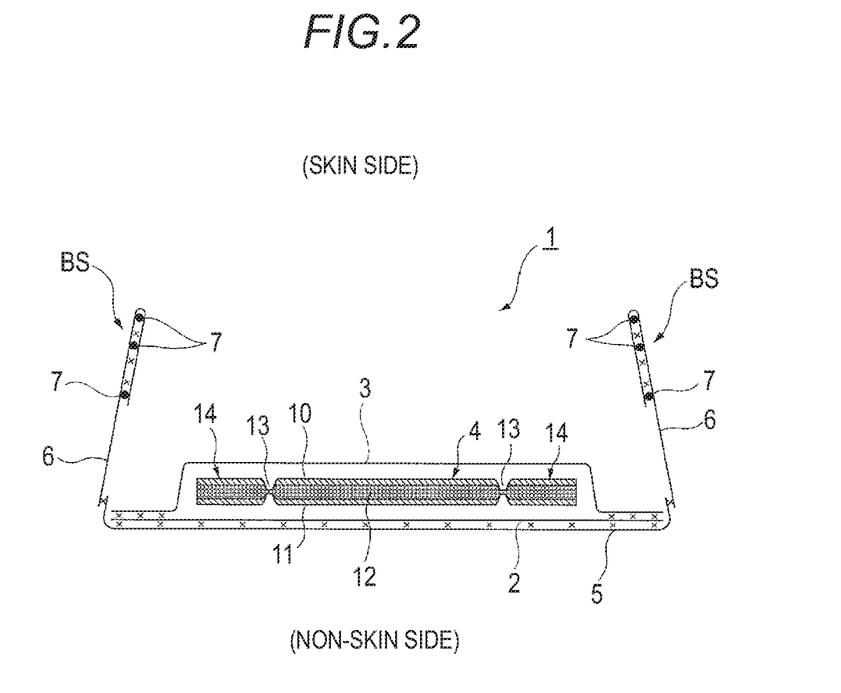
FIG. 2 is a diagram taken along the line II-II of FIG. 1.
Figure 3:
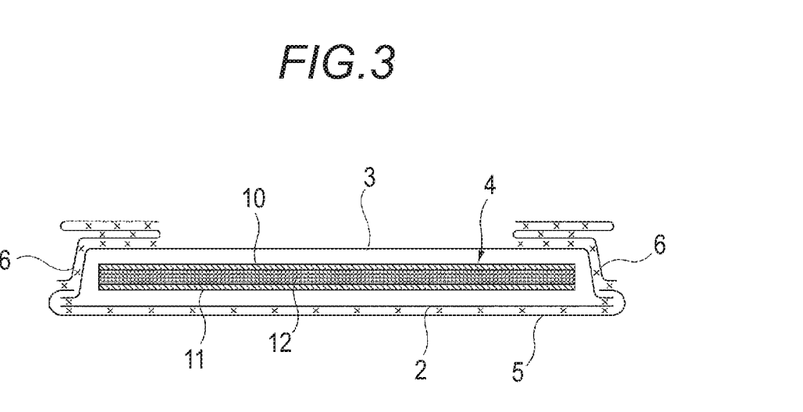
FIG. 3 is a diagram taken along the line III-III of FIG. 1.

A pad 1 according to the invention is a pad such as a urine absorbing pad used by being attached to a skin-contact surface of underwear, a disposable diaper, etc., and mainly includes, as illustrated in FIG. 1 to FIG. 3, a leakage prevention sheet 2 made of a polyethylene sheet, etc., a face sheet 3 that forms a skin-contact surface and rapidly transmits urine, etc., a polymer sheet 4 interposed between these sheets 2 and 3, an outer sheet 5 that covers an outermost surface (non-skin-contact surface) of the pad 1, and side nonwoven fabrics 6 and 6 using substantially side edge portions of the polymer sheet 4 as standing base edges and forming a pair of left and right three-dimensional gathers BS and BS provided to protrude to a skin side within a predetermined section in a front-back direction including at least a urinating part of a wearer. Further, around the polymer sheet 4, at upper and lower end edge portions thereof, outer edge portions of the leakage prevention sheet 2, the face sheet 3, and the outer sheet 5 are bonded by bonding means such as an adhesive such as hot melt, heat seal, or ultrasonic seal. In addition, at both side edge portions thereof, the leakage prevention sheet 2, the face sheet 3, the outer sheet 5, and the side nonwoven fabric 6 laterally extending from the polymer sheet 4 are bonded by bonding means such as an adhesive such as hot melt, heat seal, or ultrasonic seal.

As the leakage prevention sheet 2, a sheet material having at least a water-blocking property such as polyethylene is used. However, in recent years, a sheet having moisture permeability tends to be used from a viewpoint of preventing stuffiness. As this water blocking and moisture-permeable sheet material, a microporous sheet obtained by melt kneading an inorganic filler in an olefin resin such as polyethylene or polypropylene to form a sheet, and then monoaxially or biaxially stretching the sheet is preferably used. As the leakage prevention sheet 2, a poly-laminated nonwoven fabric obtained by laminating a plastic film and a nonwoven fabric may be used.

Next, as the face sheet 3, a perforated or non-perforated nonwoven fabric, a porous plastic sheet, etc. is preferably used. As a material fiber included in the nonwoven fabric, it is possible to use a synthetic fiber such as a polyolefin-based fiber such as polyethylene or polypropylene, a polyester-based fiber, or a polyamide-based fiber, a regenerated fiber such as rayon or cupra, and a natural fiber such as cotton, and it is possible to use a nonwoven fabric obtained by an appropriate processing method such as a spun lace method, a spun bond method, a thermal bond method, a melt blown method, or a needle punch method. Among these processing methods, the spun lace method is excellent in flexibility and drapability, and the thermal bond method is excellent in bulkiness and high compression recovery. When a large number of through-holes are formed in the face sheet 3, the body fluid is quickly absorbed, and a dry touch property is excellent. A fiber of the nonwoven fabric may be a long fiber or a short fiber, and the short fiber is preferably used to give texture of a towel cloth. In addition, to facilitate an embossing treatment, it is preferable to use an olefin-based fiber having a relatively low melting point such as polyethylene or polypropylene. In addition, it is possible to preferably use a composite fiber of a core-sheath type fiber having a fiber having a high melting point as a core and a fiber having a low melting point as a sheath, a side-by-side type fiber, or a split type fiber.

The outer sheet 5 covers the leakage prevention sheet 2 to make an outer surface of the incontinence pad 1 look and feel like a cloth. The outer sheet 5 is preferably formed using a nonwoven fabric. As a material fiber, it is possible to use a synthetic fiber such as a polyolefin-based fiber such as polyethylene or polypropylene, a polyester-based fiber, or a polyamide-based fiber, a regenerated fiber such as rayon or cupra, and a natural fiber such as cotton. As a processing method, it is possible to use a spun lace method, a spun bond method, a thermal bond method, an air through method, a needle punch method, etc. However, in terms of achieving both texture and strength, it is preferable to use a long-fiber nonwoven fabric such as a spun bond nonwoven fabric, an SMS nonwoven fabric, or SMMS nonwoven fabric.

The nonwoven fabric may be used as a single sheet, or may be used by stacking a plurality of sheets. When the plurality of sheets is stacked and used, it is preferable that the nonwoven fabrics are fixed to each other via an adhesive such as hot melt. In addition, when a nonwoven fabric is used, a fiber basis weight thereof is preferably 10 to 50 $g/m^2$, and particularly preferably 15 to 30 $g/m^2$.

One or a plurality of temporary fixing layers (not illustrated) may be provided on a non-use surface side (outer surface) of the outer sheet 5, and the pad 1 is fixed to underwear, a disposable diaper, etc. during wearing on a body. As the temporary fixing layer, a mechanical bonding type hook material may be used, or an adhesive may be used.

In the illustrated example, the outer sheet 5 is made slightly wider than a width of the polymer sheet 4, and both side portions are extended to a skin side of the face sheet 3 so that side edges of the leakage prevention sheet 2 and the face sheet 3 are rolled up. Further, on outer sides of the face sheet 3 in the width direction, side nonwoven fabrics 6 extending from surfaces of both side portions of the face sheet 3 to outer surface sides of the outer sheet 5 extending to the skin side, specifically, side nonwoven fabrics 6 configured using a nonwoven fabric material subjected to an appropriate water repellent treatment or hydrophilic treatment to prevent penetration of urine or enhance texture are arranged. As such side nonwoven fabrics 6, it is possible to use those formed by an appropriate processing method using a natural fiber, a synthetic fiber, a regenerated fiber, etc. as a material. It is preferable to use a nonwoven fabric having a reduced basis weight and air permeability in order to eliminate a feeling of stiffness and prevent stuffiness. Specifically, it is preferable to use a nonwoven fabric having a basis weight of 13 to 23 $g/m^2$. Further, to prevent permeation of the body fluid, a water-repellent nonwoven fabric coated with a silicone-based, paraffin-based, or alkylchromic chloride-based water repellent is preferably used.

An inner side portion of each of the side nonwoven fabrics 6 is folded back substantially double, and one or a plurality of (three in the illustrated example) thread-shaped elastically stretchable members 7, 7, ... whose both ends or appropriate position in a longitudinal direction is fixed to an intermediate position in a height direction are arranged inside the double sheet in a state in which the both ends or the appropriate position in the longitudinal direction is fixed. At front and back end portions, as illustrated in FIG. 3, this double sheet portion is bonded to the polymer sheet 4 side in a state of being folded back to the outer side once and laminated. In this way, at least within a predetermined section in the front-back direction including the urinating part of the wearer, as illustrated in FIG. 2, the three-dimensional gathers BS and BS standing up to the skin side are formed in a left-right pair.

<Polymer Sheet>

The polymer sheet 4 interposed between the leakage prevention sheet 2 and the face sheet 3 has a structure in which the superabsorbent polymer 12 is disposed between two nonwoven fabric sheets 10 and 11, and has a property of absorbing and retaining a body fluid. The nonwoven fabric sheet includes the nonwoven fabric sheet 10 disposed on the skin side and the nonwoven fabric sheet 11 disposed on the non-skin side.

As the nonwoven fabric sheets 10 and 11, a perforated or non-perforated nonwoven fabric is used. As a material fiber included in the nonwoven fabric, for example, in addition to a synthetic fiber such as a polyolefin-based fiber such as polyethylene or polypropylene, a polyester-based fiber, or a polyamide-based fiber, it is possible to adopt a regenerated fiber such as rayon or cupra, and a hydrophilic cellulosic fiber. Examples of the hydrophilic cellulosic fiber include a naturally derived fiber such as a cotton fiber or a pulp fiber, and an artificial cellulosic fiber such as a rayon fiber, an acetate fiber, or a lyocell fiber. As the cotton fiber, it is possible to use all cotton fibers such as raw cotton of arboreous cotton, a refined and bleached cotton fiber, a cotton fiber subjected to dyeing after being refined and bleached, a refined and bleached absorbent cotton fiber, and wool defibrated from yarn or cloth. However, to enhance an absorption speed and diffusibility of a liquid in the nonwoven fabric sheets 10 and 11, it is particularly preferable to use absorbent cotton obtained by defatting the natural fat and oil of cotton wax attached to a surface of the cotton fiber. There is no limitation on a processing method of the nonwoven fabric. However, to prevent the superabsorbent polymer 12 from falling off, it is preferable to use a processing method such as an air through method, a spun bond method, a melt blown method, or a needle punch method in which the fiber density of an obtained product is increased. In particular, the air through method, which can increase the bulk, is desirable.

A basis weight of the nonwoven fabric sheets 10 and 11 is preferably 15 $g/m^2$ or more, and particularly preferably 40 to 150 $g/m^2$.

At least the nonwoven fabric sheet 10 disposed on the skin side is made of a hydrophilic material. On the other hand, the nonwoven fabric sheet 11 disposed on the non-skin side can be made of a hydrophilic or hydrophobic material.

The superabsorbent polymer 12 includes "powder" in addition to "particles". As the superabsorbent polymer 12, it is possible to use those having a particle size used in this type of absorbent article without change, and it is desirable that those having an average particle size of 1,000 μm or less, preferably a particle size of 106 μm or more before absorption account for 99% by weight or more of the whole, and particularly those having 150 to 850 μm account for 99% by weight or more of the whole. The average particle size before absorption is preferably about 250 to 500 μm. In addition, it is desirable that an average particle size of the superabsorbent polymer 12 after absorption is three times or more of the average particle size before absorption, specifically 500 μm or more. Note that the average particle size of the superabsorbent polymer 12 before absorption means a particle size at an integrated value of 50% in a weight-based particle size distribution. The weight-based particle size distribution in this case is measured in accordance with JISZ8815-1994. In more detail, the weight-based particle size distribution is measured by stacking sieves having an inner diameter of 150 mm, a depth of 45 mm, and apertures of 710 μm, 500 μm, 300 μm, 150 μm, and 106 μm with a sieve having a narrower aperture on a lower side, putting 50 g of a measurement sample on the 710 μm sieve having a widest aperture at a top, performing sieving using a sieving machine for 10 minutes, measuring a weight of the measurement sample left on each sieve, and obtaining a weight % of the measurement sample left on each sieve based on a first weight of the measurement sample.

A basis weight amount of the superabsorbent polymer 12 can be appropriately determined according to an absorption amount required for use of the polymer sheet. Therefore, even though it cannot be generally stated, the basis weight amount can be set to 50 to 350 $g/m^2$. When the basis weight amount of the polymer is less than 50 $g/m^2$, it becomes difficult to ensure the absorption amount. When the basis weight amount exceeds 350 $g/m^2$, not only the effect is saturated, but also an excessively high amount of the superabsorbent polymer gives a gritty feeling.

The superabsorbent polymer 12 can be disposed between the two nonwoven fabric sheets 10 and 11 in a known mode. For example, it is possible to use (1) a mode in which a base sheet is arranged in a stacking recessed portion of a stacking drum using a stacking device for a superabsorbent polymer, the superabsorbent polymer is stacked on the base sheet while applying a suction force from the inside of the stacking drum in the stacking recessed portion, and then the base sheet is disposed between the two nonwoven fabric sheets 10 and 11, (2) a mode in which particles of the superabsorbent polymer 12 are bonded to the two nonwoven fabric sheets 10 and 11 by a hot melt adhesive layer, (3) a mode in which a slurry-like dispersion containing a superabsorbent polymer is applied to a surface of a base sheet and dried, and then the base sheet is disposed between the two nonwoven fabric sheets 10 and 11, etc.

Figure 4:
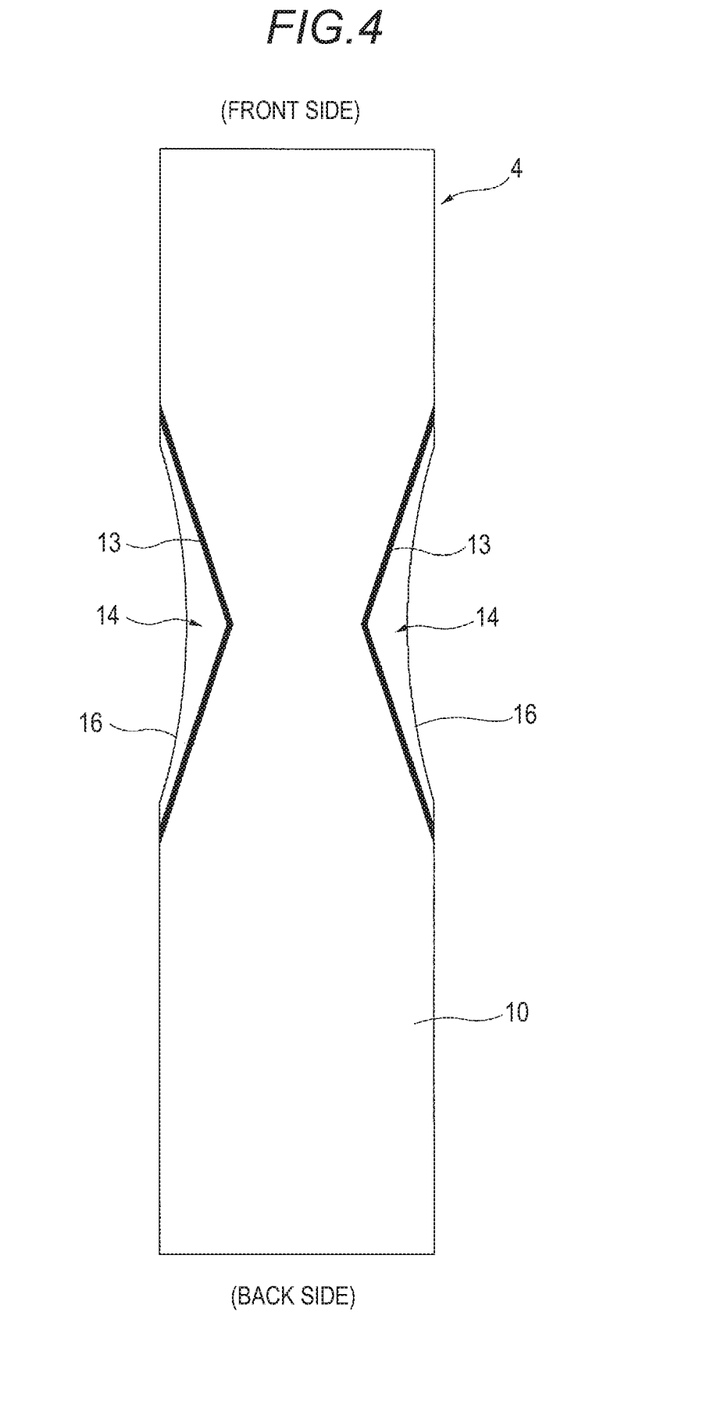
FIG. 4 is a plan view of a polymer sheet 4.

As illustrated in FIG. 4, planar-shaped continuous linear embossed grooves 13 protruding inward in a width direction from each of both side edges are formed at positions of the polymer sheet 4 with which the groin of the wearer comes into contact during wearing. The positions with which the groin of the wearer comes into contact refer to positions on both sides where around-leg cut lines 16 (see FIG. 4) are provided when the around-leg cut lines 16 are provided on the polymer sheet 4, and refer to positions on both sides of a central section obtained by dividing the polymer sheet 4 into three equal parts in the longitudinal direction when the around-leg cut lines 16 are not provided.

As illustrated in FIG. 2, the embossed grooves 13 are recessed grooves obtained by compressing each of the nonwoven fabric sheet 10 on the skin side and the nonwoven fabric sheet 11 on the non-skin side from an outer surface side and applying heat or ultrasonic waves thereto to perform a sealing process, so that the sheets are hollowed in the thickness direction. The embossed grooves 13 are provided in a pair of left and right disposed on both side portions of the polymer sheet 4, respectively, and each of the embossed grooves 13 is formed in a planar shape protruding inward in the width direction from each of the side edges of the polymer sheet 4. More specifically, a planar shape of one of the embossed grooves 13 extends obliquely backward on the inner side in the width direction from one side edge of the polymer sheet 4 on the front side of the wearer to a position corresponding to a crotch of the wearer in a middle part in the width direction not reaching a center in the width direction, and continuously extends obliquely backward on the outer side in the width direction from the position corresponding to the crotch of the wearer to one side edge of the polymer sheet 4 on the back side of the wearer. Note that the embossed grooves 13 may be recessed only from the outer surface side of the nonwoven fabric sheet 10 on the skin side and not be recessed from the outer surface side of the nonwoven fabric sheet 11 on the non-skin side, or may be recessed only from the outer surface side of the nonwoven fabric sheet 11 on the non-skin side and not be recessed from the outer surface side of the nonwoven fabric sheet 10 on the skin side.

In the illustrated example, the embossed grooves 13 include recessed grooves continuously recessed along a groove direction. However, the embossed grooves 13 may include discontinuous recessed grooves in which recessed compression portions and non-compression portions that are not recessed are alternately disposed.

Figure 5:
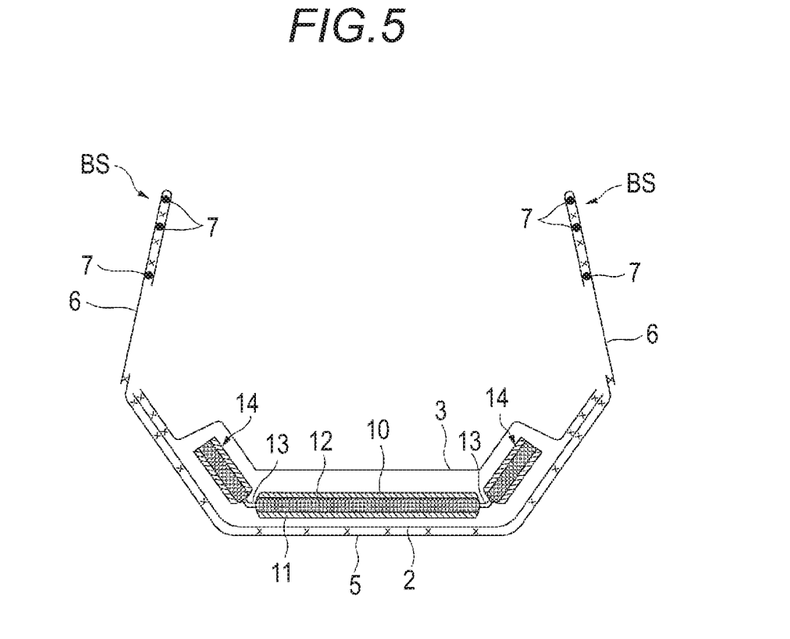
FIG. 5 is a transverse cross-sectional view (view taken along the line II-II of FIG. 1) of the pad 1 illustrating a worn state.

By providing the embossed grooves 13, as illustrated in FIG. 5, the both side portions of the polymer sheet 4 are easily deformed around the legs using the embossed grooves 13 as flexible shafts, the polymer sheet 4 easily fit around the legs during wearing, and the fit is improved. That is, when regions 14 surrounded by the embossed grooves 13 stand up to the skin side as illustrated in FIG. 5, parts standing up to the skin side adhere to an inside of the groin of the wearer, and a fit state around the legs can be maintained by following movement of the legs.

In addition, by providing the embossed grooves 13, the superabsorbent polymer 12 is stably held between the two nonwoven fabric sheets 10 and 11 in a part where movement around the legs is intense, and thus it is possible to greatly reduce spilling of the superabsorbent polymer 12 from the side edges of the polymer sheet 4 around the legs.

Further, in the pad 1, since the three-dimensional gathers BS and BS standing up to the skin side along the longitudinal direction are provided at both side portions on the skin side, respectively, deformation of the both side portions of the polymer sheet 4 using the embossed grooves 13 as flexible shafts easily occurs as illustrated in FIG. 5 due to a contraction force of the thread-shaped elastically stretchable members 7, 7, ... arranged in the three-dimensional gather BS. That is, in addition to the pressure of the groin acting from both sides toward the inside, a tensile force to the skin side by the three-dimensional gather BS acts, and thus the regions surrounded by the embossed grooves 13 easily rise to the skin side.

In the example illustrated in FIG. 4, the superabsorbent polymer 12 is disposed in the regions 14 surrounded by the embossed grooves 13 on both sides of the polymer sheet 4. That is, the superabsorbent polymer 12 is disposed on almost the entire surface between the two nonwoven fabric sheets 10 and 11. For this reason, the absorption capability of the polymer sheet 4 is improved, and more body fluid can be absorbed and retained. In addition, since the absorption capability can be exhibited even in the regions 14 surrounded by the embossed grooves 13, the leakage around the legs can be reliably prevented. Note that the inside of the region 14 is divided by the embossed groove 13 to prevent the superabsorbent polymer 12 from moving beyond the embossed groove 13 to the outside, and thus the amount of the superabsorbent polymer 12 spilling from the end edge of the region 14 can be reduced.

Figure 6:
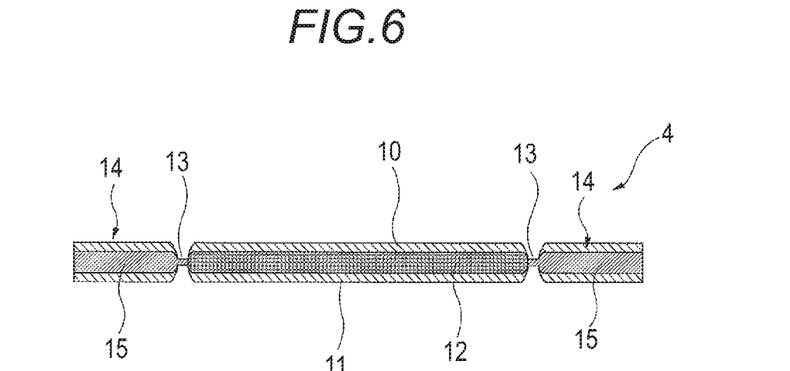
FIG. 6 is a cross-sectional view of a polymer sheet 4 according to a modification.

Meanwhile, as illustrated in FIG. 6, in the regions 14 surrounded by the embossed grooves 13 on both sides of the polymer sheet 4, a middle-layer nonwoven fabric sheet 15 may be disposed between the two nonwoven fabric sheets 10 and 11 without disposing the superabsorbent polymer 12. As the middle-layer nonwoven fabric sheet 15, it is possible to use a base sheet on which the superabsorbent polymer 12 is fixed. That is, while fixing the superabsorbent polymer 12 to a region other than the regions 14 surrounded by the embossed grooves 13 using the base sheet having substantially the same as that of the two nonwoven fabric sheets 10 and 11, the superabsorbent polymer 12 may not be fixed to the regions 14 surrounded by the embossed grooves 13. In this way, while maintaining a cushioning property in the regions 14 surrounded by the embossed grooves 13, it is possible to more reliably prevent the superabsorbent polymer 12 from falling off from the periphery of the leg.

Figure 7:
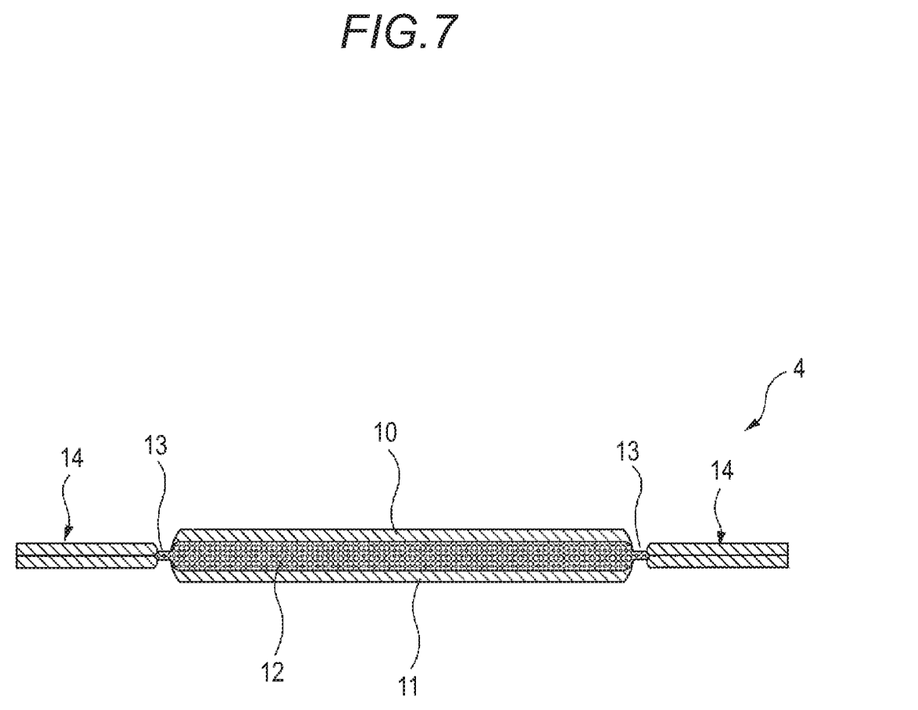
FIG. 7 is a cross-sectional view of the polymer sheet 4 according to the modification.

In addition, as illustrated in FIG. 7, in the regions 14 surrounded by the embossed grooves 13 on both sides of the polymer sheet 4, it is possible to adopt a structure in which the two nonwoven fabric sheets 10 and 11 are directly bonded by a hot melt adhesive, etc. without disposing the superabsorbent polymer 12. That is, the superabsorbent polymer 12 is disposed only in a region other than the regions 14 surrounded by the embossed grooves 13, and no member interposed between the two nonwoven fabric sheets 10 and 11 in the regions 14 surrounded by the embossed grooves 13. In this way, the regions 14 surrounded by the embossed grooves 13 are easily deformed, and the skin contact of the regions 14 is softened, so that the superabsorbent polymer 12 can be prevented from falling out of the regions 14.

In the example illustrated in FIG. 4, the around-leg cut lines 16 notched on both side portions of the polymer sheets 4 are provided in the regions 14 surrounded by the embossed grooves 13 on both sides of the polymer sheet 4. That is, the embossed grooves 13 are formed inside the around-leg cut lines 16 to surround the around-leg cut lines 16 at a predetermined distance. The around-leg cut lines 16 are shape lines along the side edges of the polymer sheet 4 in portions obtained by notching the side edge portions of the polymer sheet 4 along the legs of the wearer in a part corresponding to the crotch of the wearer. By providing the around-leg cut lines 16, the regions 14 surrounded by the embossed grooves 13 are easily fit around the legs of the wearer more favorably, and the discomfort during wearing can be reduced. In addition, since the around-leg cut lines 16 are provided in the regions 14 surrounded by the embossed grooves 13, it is possible to greatly reduce spilling of the superabsorbent polymer 12 from cut surfaces of the around-leg cut lines 16. The around-leg cut lines 16 are preferably formed by curves protruding inward in the width direction. A separation distance between the embossed grooves 13 and the around-leg cut lines 16 is 5 mm or more and 50 mm or less, preferably 5 mm or more and 30 mm or less, from a viewpoint of preventing spilling of the superabsorbent polymer 12 and improving fit around the legs.

Figure 8:
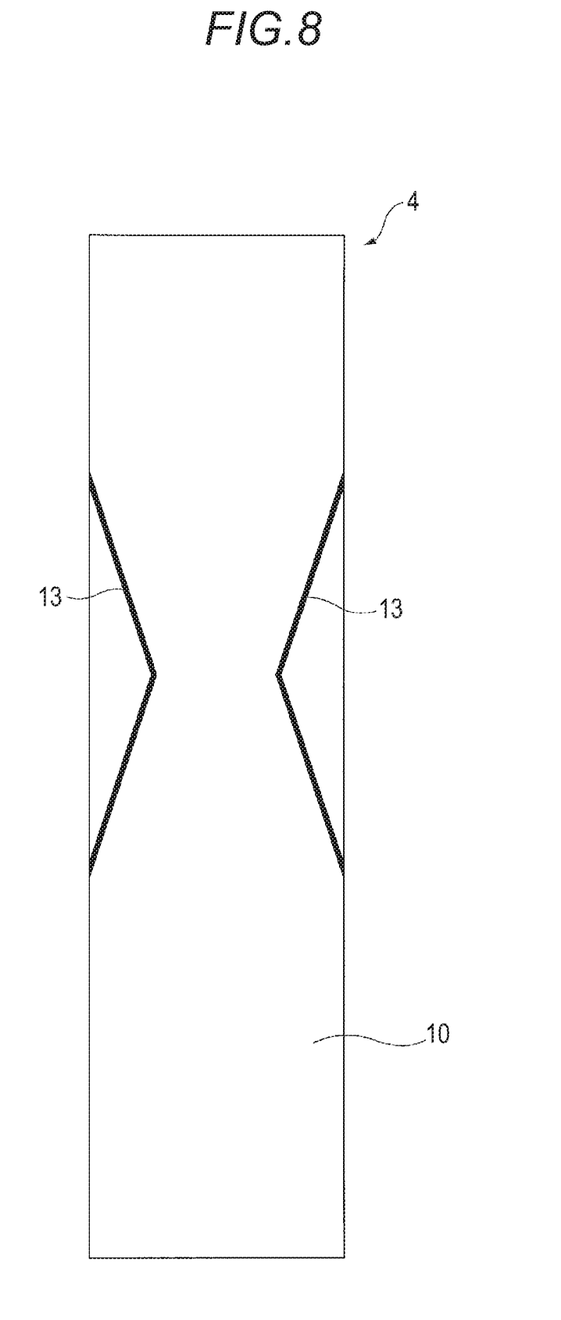
FIG. 8 is a plan view of the polymer sheet 4 according to the modification.

Meanwhile, as illustrated in FIG. 8, the around-leg cut lines 16 may not be provided. That is, the side edges of the polymer sheet 4 may be formed as straight lines in the regions surrounded by the embossed grooves 13 and straight lines in other regions substantially coincide with each other. The polymer sheet 4 is configured such that the regions surrounded by the embossed grooves 13 easily stand up to the skin side using the embossed grooves 13 as flexible shafts, and thus has a structure easily sufficiently fit around the legs even when the around-leg cut lines are not provided. In this case, to enhance the flexibility around the legs, the regions surrounded by the embossed grooves 13 preferably have a structure in which the two nonwoven fabric sheets 10 and 11 are directly bonded together without providing the superabsorbent polymer 12 as illustrated in FIG. 7.

Figure 9:
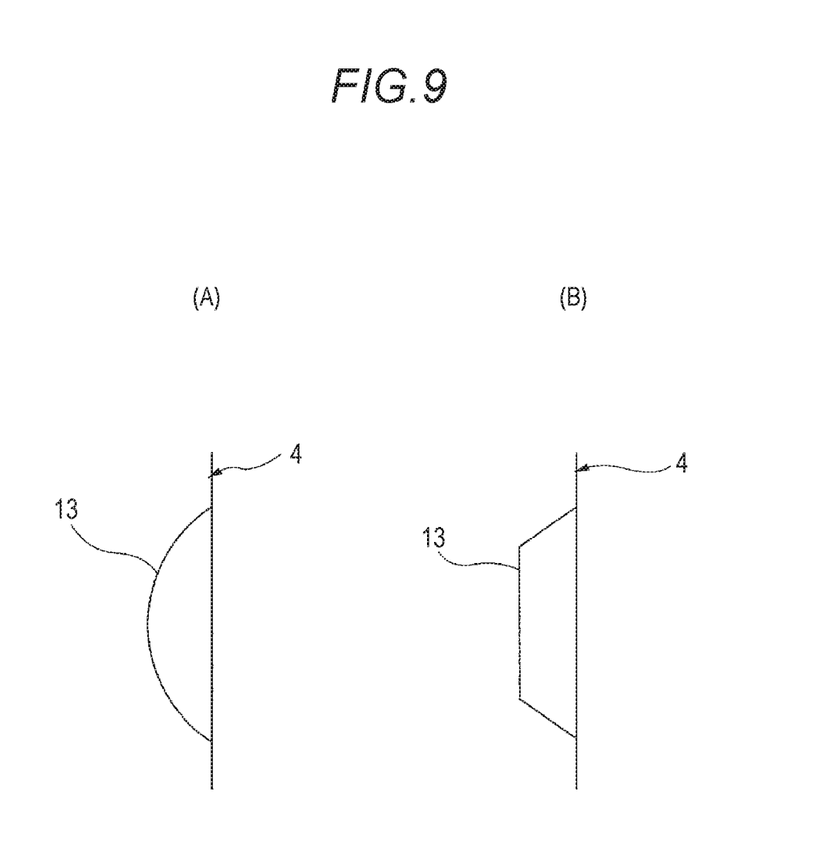
FIG. 9 is a plan view of an embossed groove 13 according to the modification.

The planar shape of the embossed grooves 13 is not particularly limited as long as the regions 14 surrounded by the embossed grooves 13 have a shape fit around the legs. For example, the planar shape may be a triangular shape protruding inward in the width direction as illustrated in FIG. 4, a curved shape protruding inward in the width direction as illustrated in FIG. 9(A), or a trapezoidal shape protruding inward in the width direction as illustrated in FIG. 9(B). Of these shapes, the regions 14 surrounded by the embossed grooves 13 are preferably formed in the triangular shape illustrated in FIG. 4 so that the regions 14 can be reliably raised to the skin side using the crotch portion as a base point.

The invention claimed is:

1. An absorbent article comprising:

a polymer sheet in which a superabsorbent polymer is disposed between two nonwoven fabric sheets in an intermediate portion in a widthwise direction, wherein linear embossed grooves having a planar shape protruding inward in a width direction from both side edges, respectively, are formed at positions of the polymer sheet with which a groin of a wearer comes into contact during wearing:, wherein the intermediate portion in the widthwise direction is surrounded, on a first side and a second side in the widthwise direction, with a first region and a second region, the first region disposed on an opposite side of a first linear embossed groove from the intermediate portion and the second region disposed on an opposite side of a second linear embossed groove from the intermediate portion, wherein the superabsorbent polymer is provided only in the intermediate portion and wherein a middle-layer nonwoven fabric sheet is provided between the two nonwoven fabric sheets in each of the first region and the second region and not in the intermediate portion.

2. The absorbent article according to claim 1, wherein three-dimensional gathers standing up to a skin side along a longitudinal direction are provided at both side portions on a skin side.

3. The absorbent article according to claim 1, wherein in regions surrounding the embossed grooves on both sides of the polymer sheet, respectively, around-leg cut lines notched on both side portions of the polymer sheets are provided.

4. The absorbent article according to claim 2, wherein in regions surrounded by the embossed grooves on both sides of the polymer sheet, respectively, around-leg cut lines notched on both side portions of the polymer sheets are provided.

* * * * *